(12) United States Patent
Rohringer et al.

(10) Patent No.: US 6,458,169 B2
(45) Date of Patent: *Oct. 1, 2002

(54) FLUORESCENT WHITENING AGENTS

(75) Inventors: Peter Rohringer, Schönenbuch (CH); Georges Metzger, Moernach (FR); Dieter Reinehr, Kandern (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 54 days.

This patent is subject to a terminal disclaimer.

(21) Appl. No.: 09/767,112

(22) Filed: Jan. 22, 2001

Related U.S. Application Data

(62) Division of application No. 09/381,468, filed as application No. PCT/EP98/01495 on Mar. 14, 1998, now Pat. No. 6,210,449.

(30) Foreign Application Priority Data

Mar. 25, 1997 (GB) .............................................. 9706110
May 17, 1997 (GB) .............................................. 9709980

(51) Int. Cl.$^7$ ......................... C07D 251/00; C09B 23/00
(52) U.S. Cl. ........................... 8/648; 8/919; 544/193.2; 427/411; 427/412
(58) Field of Search ................... 8/648, 919; 544/193.2; 427/411, 412

(56) References Cited

U.S. PATENT DOCUMENTS

| 3,420,821 A | 1/1969 | Schinzel et al. ............. 260/240 |
| 4,271,395 A | 6/1981 | Brinkmann et al. ........ 331/94.5 |

FOREIGN PATENT DOCUMENTS

| DE | 20794 | 2/1961 |
| EP | 0728749 | 8/1996 |
| GB | 1008457 | 10/1965 |
| GB | 1021527 | 3/1966 |
| GB | 1238833 | 7/1971 |
| GB | 2313850 | 12/1997 |
| JP | 63-282382 | * 11/1988 |
| WO | 9600221 | 1/1996 |
| WO | 9746541 | 12/1997 |

OTHER PUBLICATIONS

Derwent Abstr. 89–004065 for JP 63282382 (1988).
Patent Abstracts of Japan vol. 011, No. 322 (1987) for JP 62106965.
Chem. Abstr. vol. 52, No. 10, 10595h for JP 00006643 (1957).
Chem. Abstr. 71:126005q for NL 6714386 (1969).
Chem. Abstr. vol. 75, No. 6, 37928h for JP 71010076 (1968).

* cited by examiner

Primary Examiner—John Hardee
(74) Attorney, Agent, or Firm—Kevin T. Mansfield

(57) ABSTRACT

The present invention provides new compounds having the formula:

in which X is O or, preferably, NH; M is hydrogen, an alkali metal atom, ammonium or a cation formed from an amine; each $R_1$, independently, is an aminoacid residue from which a hydrogen atom on the amino group has been removed; n is 1 or 2; and each $R_2$, independently, is hydrogen, $C_1$-$C_3$alkyl, halogen, cyano, COOR in which R is hydrogen or $C_1$-$C_3$alkyl, CONH—R in which R has its previous significance, $SO_2NH$—R in which R has its previous significance, NH—COR in which R has its previous significance, $SO_3M$ in which M has its previous significance or, when n is 1, $R_2$ can also be CO—$R_3$ in which $R_3$ is $C_1$-$C_3$alkyl or phenyl;

provided that those compounds are excluded in which a) X is NH, n is 1 and $R_2$ is $SO_3M$ in which M has its previous significance; or b) X is NH, n is 2 and one $R_2$ is $SO_3M$ in which M has its previous significance, and the other $R_2$ is hydrogen, methyl or halogen; or c) X is NH, n is 1, $R_1$ is glycine and $R_2$ is H or $CO_2H$; or d) X is NH, n is 2, each $R_2$ is $SO_3M$ in which M has its previous significance and the $SO_3M$ groups are in 2,5-positions in the phenyl ring and $R_1$ is D,L-alanine, L-valine, L-leucine, L-isoleucine, L-threonine, L-aspartic acid, L-glutamic acid, L-phenylalanine, L-proline, D,L-methionine or glycine.

Most of the new class of 4,4'-diaminostilbene-2,2'-disulfonic acid compounds are useful as fluorescent whitening agents, especially for paper.

22 Claims, No Drawings

FLUORESCENT WHITENING AGENTS

This is a divisional of application Ser. No. 09/381,468, filed on Sep. 20, 1999 U.S. Pat No. 6,210,449, which is a 371 of PCT/EP98/01495, filed Mar. 14, 1998.

The present invention relates to new compounds, in particular to new 4,4'-diaminostilbene-2,2'-disulfonic acid compounds which are useful as fluorescent whitening agents or for inhibiting (quenching) the effect of anionic fluorescent whitening agents on substrates.

In WO 96/00221, there are described optical brightening agents for textiles, paper etc. The disclosed compounds have the formula:

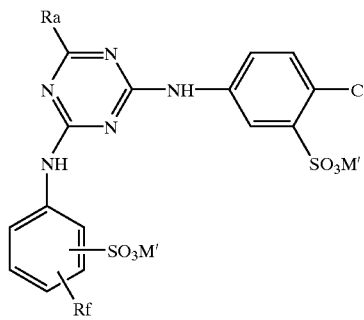

in which $R_a$ and $R_b$ are the same or different and each has the formula —$NR_cR_d$ in which $R_c$ is hydrogen; $C_1$-$C_6$alkyl which is optionally substituted by at least one of mercapto, $C_1$-$C_6$thioalkyl, OH and $SO_3M'$ in which M' is hydrogen, a colourless cation or an amine-derived cation; or —$R_e$(CO$_2$M')$_x$ in which $R_e$ is an aliphatic moiety having 1–6 carbon atoms, those valencies not bonded with groups CO$_2$M' being bonded with at least one of hydrogen, mercapto, $C_1$-$C_6$thioalkyl, OH and SO3M' in which M' has its previous significance and x is an integer from 1 to 4, provided that, when $R_c$ is $C_1$-$C_6$alkyl which is optionally substituted by at least one of mercapto, $C_1$-$C_6$thioalkyl, OH and $SO_3M'$, $R_c$ is substituted with at least both of OH and $SO_3M'$; $R_d$ is $R_c$, hydrogen or $C_3$-$C_6$alkyl, provided that $R_c$ and $R_d$ cannot both be hydrogen and that, when one of $R_c$ and $R_d$ is hydrogen, the other cannot be —(NHCH$_2$CO$_2$H); or $R_c$ and $R_d$, together with the nitrogen atom, form a ring having from 5–6 members only, one of which is heterocyclic, which ring is singly substituted with —COOM' or —$SO_3M'$; and each $R_f$, independently, is hydrogen, methyl, $C_1$-$C_6$alkoxy or halogen.

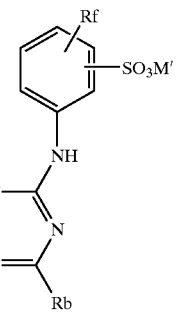

A new class of 4,4'-diaminostilbene-2,2'-disulfonic acid compounds has now been found most of which are useful as fluorescent whitening agents and which have superior properties with respect to the compounds disclosed in WO 96/00221, and others of which are useful for inhibiting (quenching) the effect of anionic fluorescent whitening agents on substrates.

Accordingly, the present invention provides new compounds having the formula:

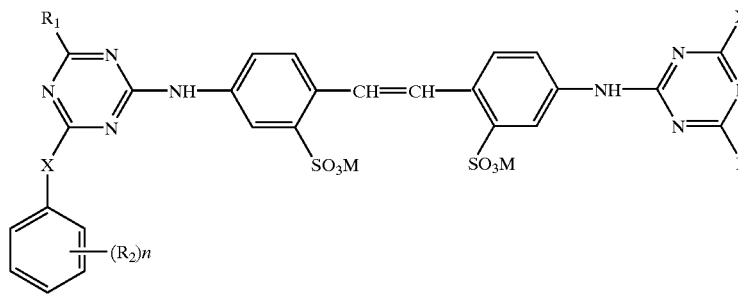

(1)

in which X is O or, preferably, NH; M is hydrogen, an alkali metal atom, ammonium or a cation formed from an amine; each $R_1$, independently, is an aminoacid residue from which a hydrogen atom on the amino group has been removed; n is 1 or 2; and each $R_2$, independently, is hydrogen, $C_1$-$C_3$alkyl, halogen, cyano, COOR in which R is hydrogen or $C_1$-$C_3$alkyl, CONH—R in which R has its previous significance, $SO_2$NH—R in which R has its previous significance, NH—COR in which R has its previous significance, $SO_3$M in which M has its previous significance or, when n is 1, $R_2$ can also be CO—$R_3$ in which $R_3$ is $C_1$-$C_3$alkyl or phenyl;
provided that those compounds are excluded in which a) X is NH, n is 1 and $R_2$ is $SO_3$M in which M has its previous significance; or
b) X is NH, n is 2 and one $R_2$ is $SO_3$M in which M has its previous significance, and the other $R_2$ is hydrogen, methyl or halogen; or
c) X is NH, n is 1, $R_1$ is glycine and $R_2$ is H or $CO_2$H; or
d) X is NH, n is 2, each $R_2$ is $SO_3$M in which M has its previous significance and the $SO_3$M groups are in 2,5-positions in the phenyl ring and $R_1$ is D,L-alanine, L-valine, L-leucine, L-isoleucine, L-threonine, L-aspartic acid, L-glutamic acid, L-phenylalanine, L-proline, D,L-methionine or glycine.

Preferably M is hydrogen, Na, K, Ca, Mg, ammonium, mono-, di-, tri- or tetra-$C_1$-$C_4$alkylammonium, mono-, di- or tri-$C_1$-$C_4$hydroxyalkylammonium or ammonium that is di- or tri-substitue with a mixture of $C_1$-$C_4$alkyl and $C_1$-$C_4$hydroxyalkyl groups. Preferably each M is Na.

A halogen substituent $R_2$ may be fluorine, bromine or iodine but is preferably chlorine.

In the compounds of formula (1), n is preferably 1 and $R_2$ is preferably hydrogen, methyl, chlorine, cyano, COOH, COO-methyl, $CONH_2$, CONH-methyl, $SO_2NH_2$, $SO_2$NH-methyl or NH'COmethyl.

Preferably, each of the aminoacid residues $R_1$ is the same. Examples of preferred aminoacid residues $R_1$ include those having the formula —NH—CH($CO_2$H)—$R_3$ in which $R_3$ is hydrogen or a group having the formula —CHR$_4$R$_5$ in which $R_4$ and $R_5$, independently, are hydrogen or $C_1$-$C_4$alkyl optionally substituted by one or two substituents selected from hydroxy, thio, methylthio, amino, carboxy, sulfo, phenyl, 4-hydroxyphenyl, 3,5-diiodo-4-hydroxyphenyl, β-indolyl, β-imidazolyl and NH=C(NH$_2$)NH—.

Specific examples of aminoacids from which such preferred aminoacid residues $R_1$ are derived include glycine, alanine, sarcosine, serine, cysteine, phenylalanine, tyrosine (4-hydroxyphenylalanine), diiodotyrosine, tryptophan (β-indolylalanine), histidine ((β-imidazolylalanine), α-aminobutyric acid, methionine, valine (α-aminoisovaleric acid), norvaline, leucine (α-aminoisocaproic acid), isoleucine (α-amino-β-methylvaleric acid), norleucine (α-amino-n-caproic acid), arginine, ornithine (α,δ-diaminovaleric acid), lysine (α,ε-diaminocaproic acid), aspartic acid (aminosuccinic acid), glutamic acid (α-aminoglutaric acid), threonine, hydroxyglutamic acid and taurine, as well as mixtures and optical isomers thereof. Of these aminoacids from which such preferred aminoacid residues $R_1$ are derived, sarcosine, taurine, glutamic acid and aspartic acid are particularly preferred.

A further preferred example of an aminoacid from which an aminoacid residue $R_1$ may be derived is iminodiacetic acid.

Other, less preferred examples of aminoacids from which aminoacid residues $R_1$ may be derived include cystine, lanthionine, proline and hydroxyproline.

In addition to the above-mentioned preferred classical aminoacids, $R_1$ may also be the residue of an aromatic aminoacid such as p-aminobenzoic acid or o-aminobenzoic acid.

In the compounds of formula (1), when n is 1 and each $R_2$ is CO—$R_3$ in which $R_3$ is $C_1$-$C_3$alkyl or phenyl, preferably methyl, such compounds are not useful as fluorescent whitening agents, rather they are are useful for inhibiting (quenching) the effect of anionic fluorescent whitening agents on substrates.

The compounds of formula (1) may be produced by reacting, under known reaction conditions, cyanuric chloride, successively, in any desired sequence, with each of 4,4'-diamino-2,2'-stilbene disulfonic acid, an amino compound capable of introducing a group

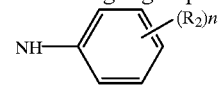

in which $R_2$ and n have their previous significance, and a compound capable of introducing a group $R_1$, in which $R_1$ has its previous significance.

The starting materials are known compounds which are readily available.

Most of the compounds of formula (1) are excellent fluorescent whitening agents for substrates such as textiles and, in particular, for paper.

Accordingly, the present invention provides a method for the fluorescent whitening of a substrate comprising contacting the substrate with a compound having the formula (1A):

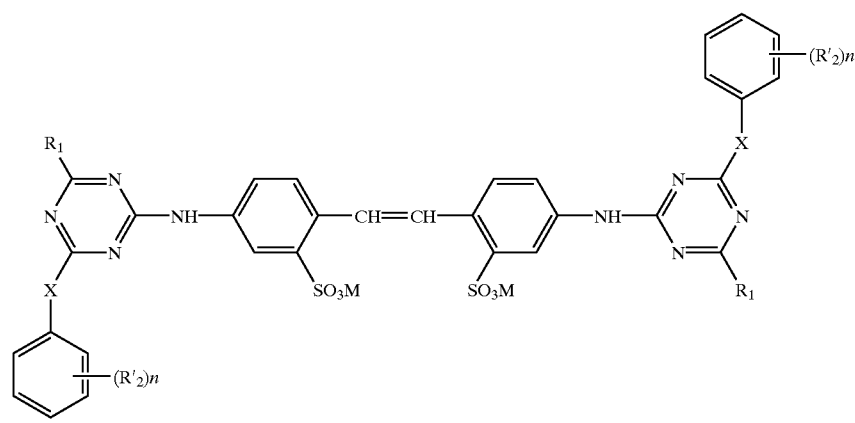

(1A)

in which X is O or NH; M is hydrogen, an alkali metal atom, ammonium or a cation formed from an amine; each $R_1$, independently, is an aminoacid residue from which a hydrogen atom on the amino group has been removed; n is 1 or 2; and each $R'_2$, independently, is hydrogen, $C_1$-$C_3$alkyl, halogen, cyano, COOR in which R is hydrogen or $C_1$-$C_3$alkyl, CONH—R in which R has its previous significance, $SO_2NH$—R in which R has its previous significance, NH—COR in which R has its previous significance or $SO_3M$ in which M has its previous significance; provided that those compounds are excluded in which X is NH, n is 2 and one $R_2$ is $SO_3M$ in which M has its previous significance, and the other $R_2$ is hydrogen, methyl or halogen.

When used for the fluorescent whitening of paper, the compound of formula (1A) according to the present invention may be applied to the paper substrate in the form of a paper coating composition, or directly in the size press.

In one preferred aspect, the present invention provides a method for the fluorescent whitening of a paper surface, comprising contacting the paper surface with a coating composition comprising a white pigment; a binder dispersion; optionally a water-soluble co-binder; and sufficient of a fluorescent whitening agent having the formula (1A) according to the present invention, to ensure that the treated paper contains 0.01 to 1% by weight, based on the white pigment, of a fluorescent whitening agent having the formula (1A).

As the white pigment component of the paper coating composition used according to the method of the present invention, there are preferred inorganic pigments, e.g., aluminium or magnesium silicates, such as China clay and kaolin and, further, barium sulfate, satin white, titanium dioxide, calcium carbonate (chalk) or talcum; as well as white organic pigments.

The paper coating compositions used according to the method of the present invention may contain, as binder, inter alia, plastics dispersions based on copolymers of butadiene/styrene, acrylonitrile/butadiene/styrene, acrylic acid esters, acrylic acid esters/styrene/acrylonitrile, ethylene/vinyl chloride and ethylene/vinyl acetate; or homopolymers, such as polyvinyl chloride, polyvinylidene chloride, polyethylene and polyvinyl acetate or polyurethanes. A preferred binder consists of styrene/butyl acrylate or styrene/butadiene/acrylic acid copolymers or styrene/butadiene rubbers. Other polymer latices are described, for example, in U.S. Pat. Nos. 3,265,654, 3,657,174, 3,547,899 and 3,240,740.

The optional water-soluble protective colloid may be, e.g., soya protein, casein, carboxymethylcellulose, natural or modified starch, chitosan or a derivative thereof or, especially, polyvinyl alcohol. The preferred polyvinyl alcohol protective colloid component may have a wide range of saponification levels and molecular weights; e.g. a saponification level ranging from 40 to 100; and an average molecular weight ranging from 10,000 to 100,000.

Recipes for coating compositions for paper are described, for example, in J. P. Casey "Pulp and Paper"; Chemistry and Chemical Technology, 2nd edition, Volume III, pages 1684–1649 and in "Pulp and Paper Manufacture", 2nd and 5th edition, Volume II, page497 (McGraw-Hill).

The paper coating compositions used according to the method of the present invention preferably contain 10 to 70% by weight of a white pigment. The binder is preferably used in an amount which is sufficient to make the dry content of polymeric compound up to 1 to 30% by weight, preferably 5 to 25% by weight, of the white pigment. The amount of fluorescent brightener preparation used according to the invention is calculated so that the fluorescent brightener is preferably present in amounts of 0.01 to 1% by weight, more preferably 0.05 to 1% by weight, and especially 0.05 to 0.6% by weight, based on the white pigment.

The paper coating composition used in the method according to the invention can be prepared by mixing the components in any desired sequence at temperature from 10 to 100° C., preferably 20 to 80° C. The components here also include the customary auxiliaries which can be added to regulate the rheological properties, such as viscosity or water retention capacity, of the coating compositions. Such auxiliaries are, for example, natural binders, such as starch, casein, protein or gelatin, cellulose ethers, such as carboxyalkylcellulose or hydroxyalkylcellulose, alginic acid, alginates, polyethylene oxide or polyethylene oxide alkyl ethers, copolymers of ethylene oxide and propylene oxide, polyvinyl alcohol, water-soluble condensation products of formaldehyde with urea or melamine, polyphosphates or polyacrylic acid salts.

The coating composition used according to the method of the present invention is preferably used to produce coated printed or writing paper, or special papers such as cardboard or photographic papers.

The coating composition used according to the method of the invention can be applied to the substrate by any conventional process, for example with an air blade, a coating blade, a roller, a doctor blade or a rod, or in the size press, after which the coatings are dried at paper surface temperatures in the range from 70 to 200° C., preferably 90 to 130° C., to a residual moisture content of 3–8%, for example with infra-red driers and/or hot-air driers. Comparably high degrees of whiteness are thus achieved even at low drying temperatures.

By the use of the method according to the invention, the coatings obtained are distinguished by optimum distribution of the dispersion fluorescent brightener over the entire surface and by an increase in the level of whiteness thereby achieved, by a high fastness to light and to elevated temperature (e.g. stability for 24 hours at 60–100° C.) and excellent bleed-fastness to water.

In a second preferred aspect, the present invention provides a method for the fluorescent whitening of a paper surface comprising contacting the paper in the size press with an aqueous solution containing a size, optionally an inorganic or organic pigment and 0.1 to 20 g/l of a fluorescent whitening agent having the formula (1A). Preferably, the size is starch, a starch derivative or a synthetic sizing agent, especially a water-soluble copolymer.

The present invention also provides, as a third aspect, a method for the improvement of the SPF of a textile fibre material, comprising treating the textile fibre material with 0.05 to 3.0% by weight, based on the weight of the textile fibre material, of one or more compounds having the formula (1A) as hereinbefore defined.

Textile fibres treated according to the method of the present invention may be natural or synthetic fibres or mixtures thereof. Examples of natural fibres include vegetable fibres such as cotton, viscose, flax, rayon or linen, preferably cotton and animal fibres such as wool, mohair, cashmere, angora and silk, preferably wool. Synthetic fibres include polyester, polyamide and polyacrylonitrile fibres. Preferred textile fibres are cotton, polyamide and wool fibres.

Preferably, textile fibres treated according to the method of the present invention have a density of less than 200 g/m² and have not been previously dyed in deep shades.

Some of the compounds of formula (1A) used in the method of the present invention may be only sparingly soluble in water and may need to be applied in dispersed form. For this purpose, they may be milled with an appropriate dispersant, conveniently using quartz balls and an impeller, down to a particle size of 1–2 microns.

As dispersing agents for such sparingly-soluble compounds of formula (1A) there may be mentioned:

- acid esters or their salts of alkylene oxide adducts, e.g., acid esters or their salts of a polyadduct of 4 to 40 moles of ethylene oxide with 1 mole of a phenol, or phosphoric acid esters of the adduct of 6 to 30 moles of ethylene oxide with 1 mole of 4-nonylphenol, 1 mole of dinonylphenol or, especially, with 1 mole of compounds which have been produced by the addition of 1 to 3 moles of styrenes on to 1 mole of phenol;
- polystyrene sulphonates;
- fatty acid taurides;
- alkylated diphenyloxide-mono- or -di-sulphonates;
- sulphonates of polycarboxylic acid esters;
- addition products of 1 to 60, preferably 2 to 30 moles of ethylene oxide and/or propylene oxide on to fatty amines, fatty amides, fatty acids or fatty alcohols, each having 8 to 22 carbon atoms or on to tri- to hexavalent $C_3$-$C_6$alkanols, the addition products having been converted into an acid ester with an organic dicarboxylic acid or with an inorganic polybasic acid;
- lignin sulphonates; and, in particular
- formaldehyde condensation products, e.g., condensation products of lignin sulphonates and/or phenol and formaldehyde; condensation products of formaldehyde with aromatic sulphonic acids, e.g., condensation products of ditolylethersulphonates and formaldehyde; condensation products of naphthalenesulphonic acid and/or naphthol- or naphthylaminesulphonic acids and formaldehyde; condensation products of phenolsulphonic acids and/or sulphonated dihydroxydiphenylsulphone and phenols or cresols with formaldehyde and/or urea; or condensation products of diphenyloxide-disulphonic acid derivatives with formaldehyde.

Depending on the type of compound of formula (1A) used, it may be beneficial to carry out the treatment in a neutral, alkaline or acidic bath. The method is usually conducted in the temperature range of from 20 to 140° C., for example at or near to the boiling point of the aqueous bath, e.g. at about 90° C.

Solutions of the compound of formula (1A), or its emulsions in organic solvents may also be used in the method of the present invention. For example, the so-called solvent dyeing (pad thermofix application) or exhaust dyeing methods in dyeing machines may be used.

If the method of the present invention is combined with a textile treatment or finishing method, such combined treatment may be advantageously carried out using appropriate stable preparations which contain the compound of formula (1A) in a concentration such that the desired SPF improvement is achieved.

In certain cases, the compound of formula (1A) is made fully effective by an after-treatment. This may comprise a chemical treatment such as treatment with an acid, a thermal treatment or a combined thermal/chemical treatment.

It is often advantageous to use the compound of formula (1A) in admixture with an assistant or extender such as anhydrous sodium sulfate, sodium sulfate decahydrate, sodium chloride, sodium carbonate, an alkali metal phosphate such as sodium or potassium orthophosphate, sodium or potassium pyrophosphate or sodium or potassium tripolyphosphate, or an alkali metal silicate such as sodium silicate.

In addition to the compounds of formula (1A), a minor proportion of one or more adjuvants may also be employed in the method of the present invention. Examples of adjuvants include emulsifiers, perfumes, colouring dyes, opacifiers, further fluorescent whitening agents, bactericides, nonionic surfactants, fabric care ingredients, especially fabric softeners, stain release or stain repellant ingredients or water-proofing agents, anti-gelling agents such as nitrites or nitrates of alkali metals, especially sodium nitrate, and corrosion inhibitors such as sodium silicate.

The amount of each of these optional adjuvants should not exceed 1%, and preferably ranges from 0.01 to 1% by weight on the treated fibre.

The method of the present invention, in addition to providing protection to the skin, also increases the useful life of a textile article treated according to the present invention. In particular, the tear resistance and/or lightfastness of the treated textile fibre material may be improved.

The present invention also provides a textile fabric produced from a fibre treated according to the method of the present invention as well as an article of clothing produced from the said fabric.

Such textile fabrics and articles of clothing produced from the said fabrics typically have an SPF rating of 20 and above whereas untreated cotton, for example, generally has an SPF rating of from 2 to 4.

The treatment method according to the present invention may also be conducted by washing the textile fibre material with a detergent containing at least one compound of formula (1A), thereby imparting an excellent sun protection factor to the fibre material so washed.

The detergent treatment according to the present invention is preferably effected by washing the textile fibre material at least once with the detergent composition at a temperature ranging from 10 to 100C., especially from 15 to 60° C.

The detergent composition used preferably comprises:

i) 5–90%, preferably 5–70% of an anionic surfactant and/or a nonionic surfactant;

ii) 5–70%, preferably 5–40% of a builder;

iii) 0–30%, preferably 1–12% of a peroxide;

iv) 0–10%, preferably 1–6% of a peroxide activator and/or 0-1%, preferably 0.1-0.3% of a bleaching catalyst;

v) 0.005–2%, preferably 0.01–1% of at least one compound of formula (1A); and vi) 0.005–10%, preferably 0.1–5% of of one or more auxiliaries, each by weight, based on the total weight of the detergent.

The said detergent compositions are also new and, as such form a further aspect of the present invention.

The detergent may be formulated as a solid, as an aqueous liquid comprising 5–50, preferably 10–35% water or as a non-aqueous liquid detergent, containing not more than 5, preferably 0–1 wt. % of water, and based on a suspension of a builder in a non-ionic surfactant, as described, e.g., in GB-A-2158454.

The anionic surfactant component may be, e.g., a sulphate, sulphonate or carboxylate surfactant, or a mixture of these.

Preferred sulphates are alkyl sulphates having 12–22 carbon atoms in the alkyl radical, optionally in combination with alkyl ethoxy sulphates having 10–20 carbon atoms in the alkyl radical.

Preferred sulphonates include alkyl benzene sulphonates having 9–15 carbon atoms in the alkyl radical.

In each case, the cation is preferably an alkali metal, especially sodium.

Preferred carboxylates are alkali metal sarcosinates of formula R-CO(R$^1$)CH$_2$COOM$^1$ in which R is alkyl or alkenyl having 9–17 carbon atoms in the alkyl or alkenyl radical, R$^1$ is C$_1$-C$_4$ alkyl and M$^1$ is alkali metal.

The nonionic surfactant component may be, e.g., a condensate of ethylene oxide with a C$_9$-C$_{15}$ primary alcohol having 3–8 moles of ethylene oxide per mole.

The builder component may be an alkali metal phosphate, especially a tripolyphosphate; a carbonate or bicarbonate, especially the sodium salts thereof; a silicate or disilicate; an aluminosilicate; a polycarboxylate; a polycarboxylic acid; an organic phosphonate; or an aminoalkylene poly (alkylene phosphonate); or a mixture of these.

Preferred silicates are crystalline layered sodium silicates of the formula NaHSi$_m$O$_{2m+1}$·pH$_2$O or Na$_2$Si$_m$O$_{2m+1}$·pH$_2$O in which m is a number from 1.9 to 4 and p is 0 to 20.

Preferred aluminosilicates are the commercially-available synthetic materials designated as Zeolites A, B, X, and HS, or mixtures of these. Zeolite A is preferred.

Preferred polycarboxylates include hydroxypolycarboxylates, in particular citrates, polyacrylates and their copolymers with maleic anhydride.

Preferred polycarboxylic acids include nitrilotriacetic acid and ethylene diamine tetra-acetic acid.

Preferred organic phosphonates or aminoalkylene poly (alkylene phosphonates) are alkali metal ethane 1-hydroxy diphosphonates, nitrilo trimethylene phosphonates, ethylene diamine tetra methylene phosphonates and diethylene triamine penta methylene phosphonates.

Any peroxide component may be any organic or inorganic peroxide compound, described in the literature or available on the market, which bleaches textiles at conventional washing temperatures, e.g. temperatures in the range of from 5° C. to 90° C. In particular, the organic peroxides are, for example, monoperoxides or polyperoxides having alkyl chains of at least 3, preferably 6 to 20, carbon atoms; in particular diperoxydicarboxylates having 6 to 12 C atoms, such as diperoxyperazelates, diperoxypersebacates, diperoxyphthalates and/or diperoxydodecanedioates, especially their corresponding free acids, are of interest. It is preferred, however, to employ very active inorganic peroxides, such as persulphate, perborate and/or percarbonate. It is, of course, also possible to employ mixtures of organic and/or inorganic peroxides. The peroxides, especially the inorganic peroxides, are preferably activated by the inclusion of an activator such as tetraacetyl ethylenediamine or nonoyloxybenzene sulfonate. Bleaching catalysts which may be added include, e.g., enzymatic peroxide precursors and/or metal complexes. Preferred metal complexes are manganese or iron complexes such as manganese or iron phthalocyanines or the complexes described in EP-A-0509787.

The detergents used will usually contain one or more auxiliaries such as soil suspending agents, for example sodium carboxymethylcellulose; salts for adjusting the pH, for example alkali or alkaline earth metal silicates; foam regulators, for example soap; salts for adjusting the spray drying and granulating properties, for example sodium sulphate; perfumes; and also, if appropriate, antistatic and softening agents; such as smectite clays; enzymes, such as amylases and proteases; photobleaching agents; pigments; and/or shading agents. These constituents should, of course, be stable to any bleaching system employed.

The following Examples further illustrate the present invention. Parts and percentages shown therein are by weight unless otherwise stated. The compound of Example 9 has been described in Chem. Abstr. 107:238581.

EXAMPLE 1

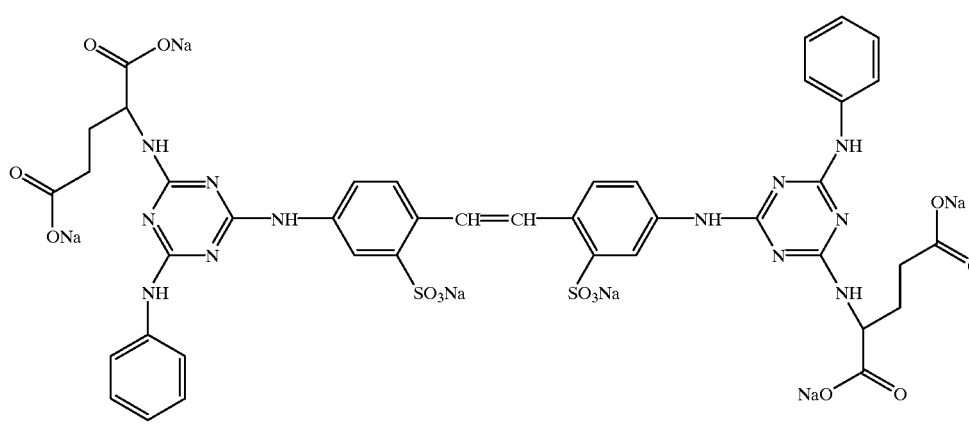

(101)

10 g of of the compound of formula:

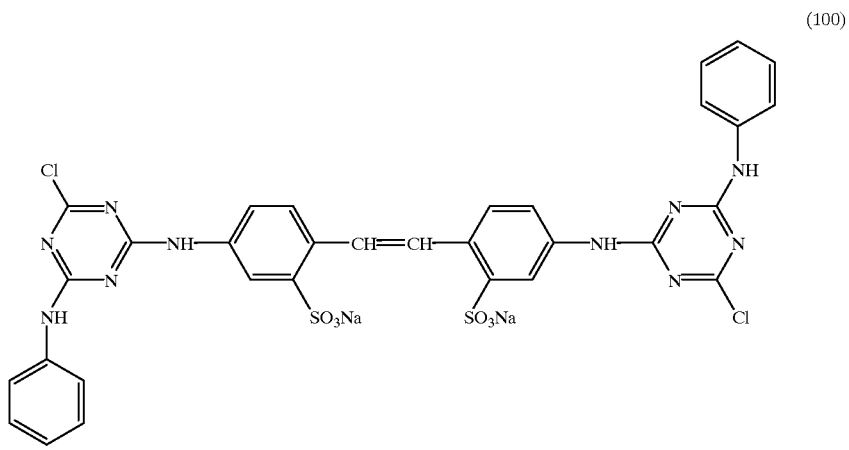

are dissolved in a mixture of 70 ml of methylcellosolve and 40 ml of water while heating the mixture in an oil bath at a bath temperature of 120° C. 7.61 g of D,L-glutamic acid are added and the mixture is stirred at this temperature for 8 hours, the pH value of the mixture being held at 8–9 during this time by the addition of sodium carbonate. The reaction is finished after 8 hours. The free acid is precipitated by treating the reaction mixture with 200 ml of acetone and 13 ml of conc. HCl. The precipitate is filtered off with suction and washed with acetone and water. The washed filtercake is suspended in 200 ml of water, brought into solution by adding sufficient 30% aqueous sodium hydroxide solution at pH 8 and then concentrated by evaporation. After drying, there remain 10.0 g (64% theory) of the compound of formula (101).

Elemental analysis of the compound having the formula (101) and having the empirical formula $C_{42}H_{34}N_{12}O_{14}S_2Na_6 \cdot 8H_2O \cdot 0.25NaCl \cdot 0.7Na_2CO_3$ gives:

Req. % C 37.55; H 3.69; N 12.31; S 4.69; $H_2O$ 10.54; $Cl^-$ 0.65

Found % C 37.13; H 3.55; N 12.57; S 4.34; $H_2O$ 10.65; $Cl^-$ 0.66.

The starting compound of formula (100) is obtained in known manner by firstly reacting cyanuric chloride with 4,4'-diamino-2,2'-stilbene disulfonic acid, and then reacting the reaction product so obtained with 1 mole of aniline.

EXAMPLE 2

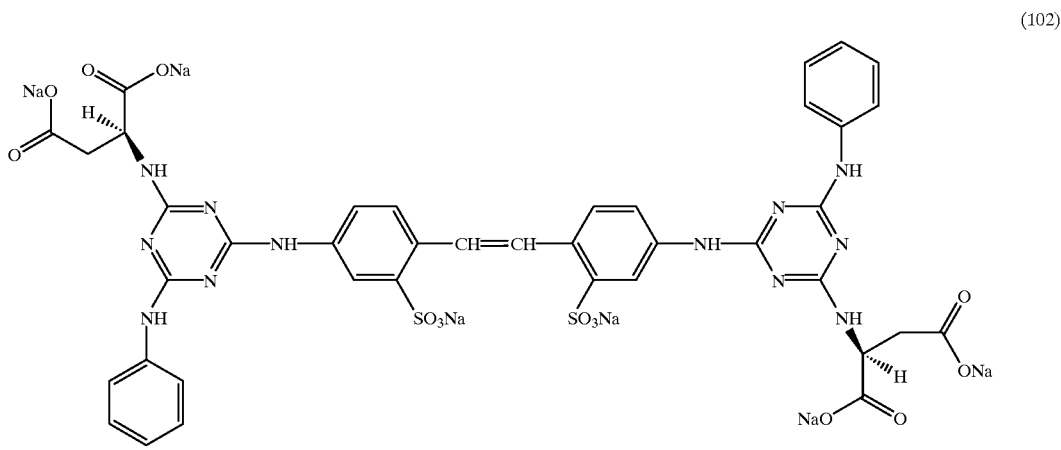

Using the procedure described in Example 1, 10 g of the compound of formula (100) are stirred with 6.92 g of D-aspartic acid for 8 hours at an oil bath temperature of 120° C. After 8 hours, HPLC analysis of the reaction mixture confirmed that the reaction was complete.

After working up the reaction mixture in the manner described in Example 1, there are obtained 10.0 g (71% theory) of the compound of formula (102).

Elemental analysis of the compound having the formula (102) and having the empirical formula $C_{40}H_{30}N_{12}O_{14}S_2Na_6 \cdot 8H_2O \cdot 1.3NaCl$. gives:

Req. % C 36.28; H 3.50; N 12.69; S 4.84; $Cl^-$ 3.48.

Found % C 36.25; H 3.59; N 12.54; S 4.76; $Cl^-$ 3.48.

EXAMPLE 3

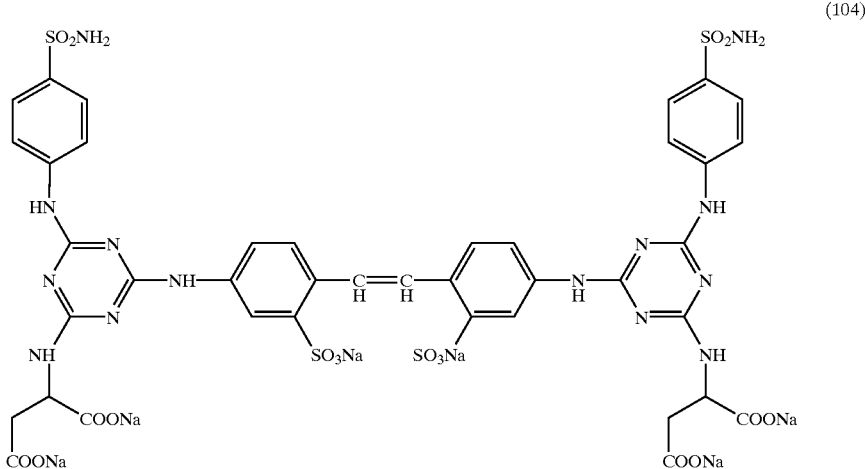

(104)

Using the procedure described in Example 1, 10 g of the compound of formula.

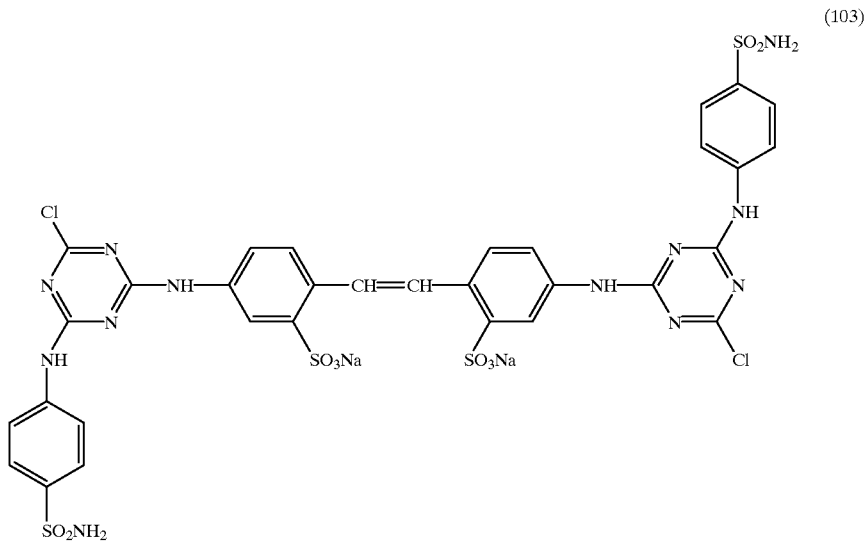

(103)

are reacted with 5.38 g of D,L-aspartic acid and the reaction product is worked up in an analogous manner. After drying, there are obtained 4 g (36% theory) of the compound of formula (104) as a white powder.

Elemental analysis of the compound having the formula (104) and having the empirical formula $C_{40}H_{32}N_{14}Na_6O_{18}S_4 \cdot 12H_2O$. gives:

Req. % C 32.48; H 3.81; N 13.25; S 8.67.
Found % C 32.30; H 3.67; N 13.07; S 8.10.

The starting compound of formula (103) is obtained in known manner by firstly reacting cyanuric chloride with 4,4'-diamino-2,2'-stilbene disulfonic acid, and then reacting the reaction product so obtained with 1 mole of 4-aminosulfonylaniline.

The compound of formula (104) imparted excellent whiteness and SPF values to cotton when applied to the cotton either by a conventional method from a long treatment bath at 100° C., or by foularding at 70° C.

EXAMPLE 4

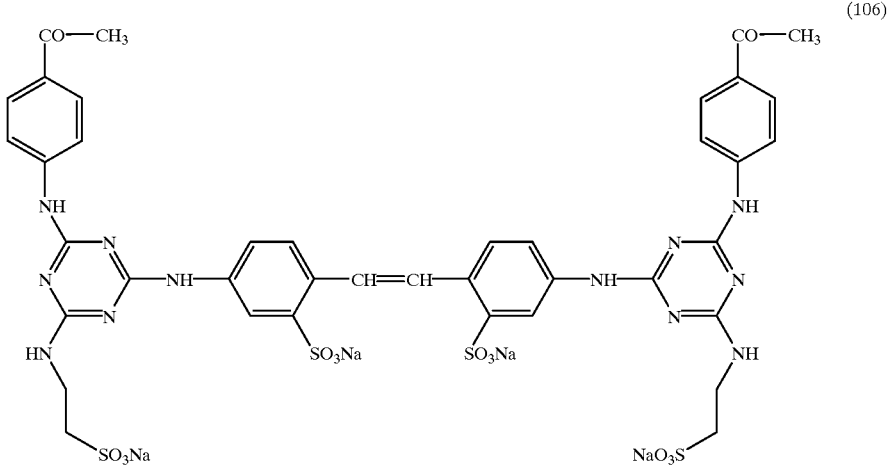
(106)

A) 18.81 g of cyanuric chloride (98% purity) are dissolved in 95 ml of acetone and poured on to 100 g of a mixture of ice and water. Over 30 minutes, a solution of 18.5 g of of diaminostilbene-di-sulfonic acid (100% purity) is added, dropwise, into 320 g of a mixture of ice and water at a temperature in the range of from −5° C. to 0° C. Finally, over 15 minutes, 50 ml of a 1 molar soda solution are added, dropwise, at this temperature, and the whole is stirred for a further 1 hour. 13.5 g of 4-aminoacetophenone are added and the mixture is heated to 50° C., over 90 minutes. During this procedure, the pH of the reaction mixture is held at 7–8 by the addition of sodium carbonate. In order to complete the reaction, the acetone is distilled off until the temperature of the reaction mixture has reached 66° C. The precipitated deposit is filtered warm with suction, washed with dilute aqueous sodium chloride (2%) and then with 300 ml of cold water. After drying, there remain 44.8 g (88% theory) of the compound of formula Req. % C 42.57; H 3.77; N 13.79.
Found % C 42.59; H 3.85; N 13.74.

B) 5 g of the compound of formula (105) obtained in part A) are suspended in 100 ml of water. 1.3 g of taurine are added and the reaction mixture is heated to 90° C. and the pH is held at 9-10 using sodium carbonate. The reactants are allowed to further react at this pH and temperature for 15 hours. Finally, the reaction mixture is concentrated and the compound (113) is precipitated with acetone. After filtration with suction, washing with acetone and drying, there remain 5.9 g (81 % theory) of the compound (113).

Elemental analysis of the compound having the formula (106) and having the empirical formula $C_{40}H_{36}N_{12}Na_4O_{14}S_4 \cdot 0.66$ NaCl. $16.5\ H_2O$ gives:

Req. % C 32.8; H 4.74; N 11.47; S 8.75; Cl 1.60; Na 7.32.
Found % C 32.7; H 4.7; N 11.5; S 9.1; Cl 1.6; Na 7.4.

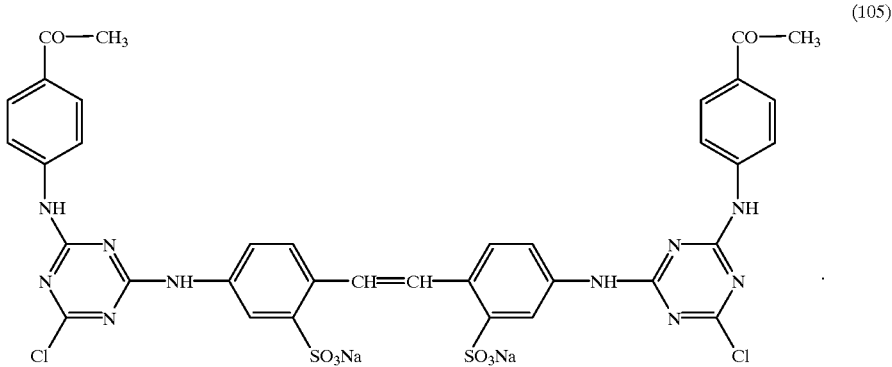
(105)

Elemental analysis of the compound having the formula (105) and having the empirical formula $C_{36}H_{26}N_{10}O_8Cl_2S_2Na_2 \cdot 6.0\ H_2O$ gives:

The compound having the formula (106) effects a significant reduction in whiteness and fluorescence of pre-brightened paper treated with said compound.

EXAMPLE 5

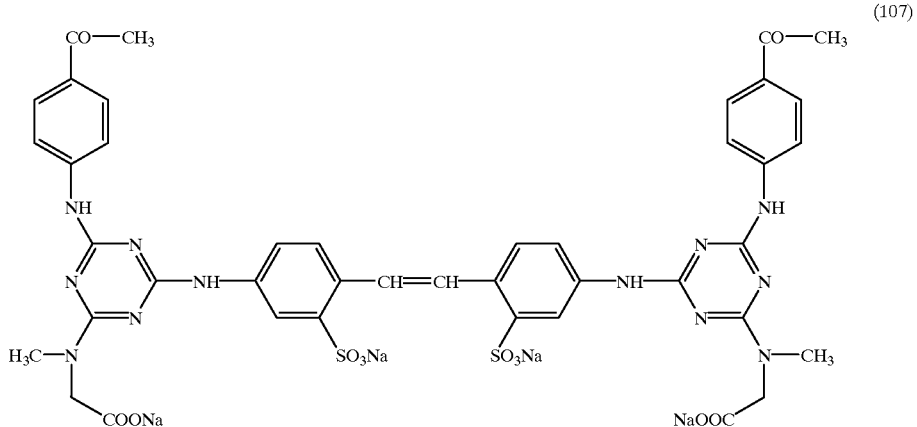
(107)

Using an analogous procedure to that described in Example 4, compound (107) is produced by reacting the compound (105) with 0.9 g of sarcosine instead of taurine. The reaction is complete after 6 hours and the yield of the compound (107) is 93% of theory.

Elemental analysis of the compound having the formula (107) and having the empirical formula $C_{42}H_{36}N_{12}Na_4O_{12}S_2$ 15 $H_2O$ gives:

Req. % C 38.02; H 5.01; N 12.66.
Found % C 38.10; H 4.87; N 12.65.

The compound having the formula (107) effects a significant reduction in whiteness and fluorescence of pre-brightened paper treated with said compound.

EXAMPLE 6

Using an analogous procedure to that described in Example 4, compound (108) is produced by reacting the compound (105) with N-methyl-ethanolamine instead of taurine. The reaction is complete after 6.5 hours and the yield of the compound (108) is 81% of theory.

The material analyzed was partly present as the N-methyl-ethanolamine salt.

Elemental analysis of the compound having the formula (108) and having the empirical formula $C_{42}H_{42}N_{12}Na_2O_{10}S_2$. 0.6 N- methyl-ethanolamine. 5 $H_2O$ gives:

Req. % C 47.0; H 5.02; N 15.78; S 5.73.
Found % C 46.75; H 4.92; N 15.46; S 5.71.

The compound having the formula (108) effects a significant reduction in whiteness and fluorescence of pre-brightened paper treated with said compound.

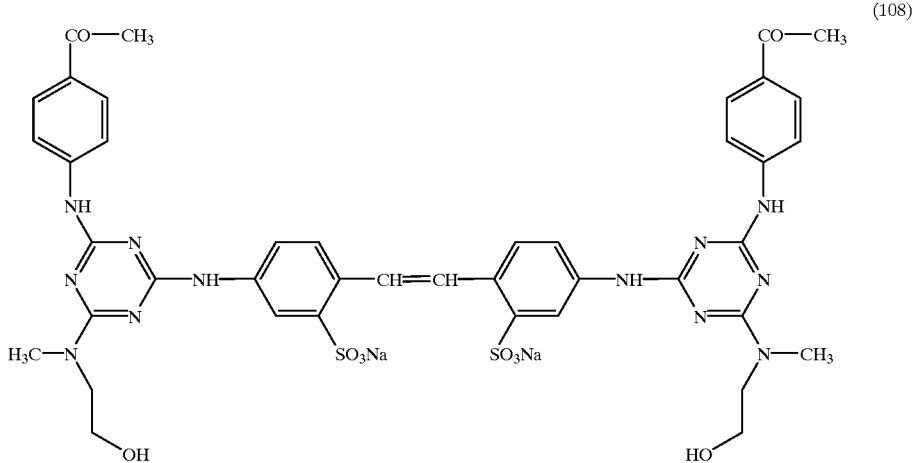
(108)

EXAMPLE 7

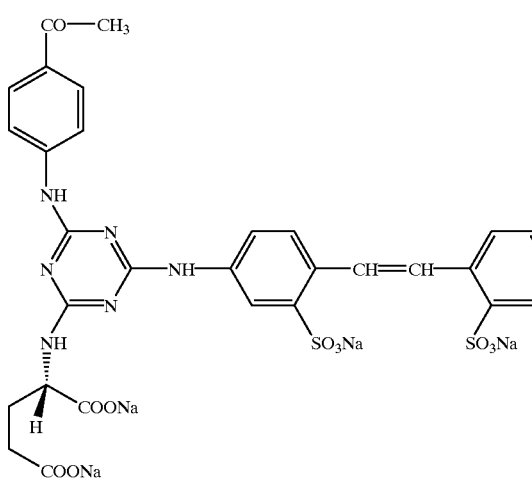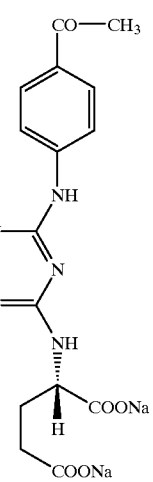

(109)

10 g of the compound of formula (105) are reacted with 5.8 g of L-glutamic acid in a 6:9 by weight mixture of water and methylcellosolve at 120° C. in an oil bath, the pH being held at 8–9 by the addition of sodium carbonate. After 6 hours, the reaction is complete. The reaction mixture is dropped into acetone acidified with HCl, whereupon the compound of formula (109) precipitates out as the free acid. After filtration with suction and washing with acetone-water, the filtercake is converted into the corresponding hexasodium salt by the addition of the calculated amount of aqueous sodium hydroxide, and evaporation to dryness. The yield is 90% of theory.

Elemental analysis of the compound having the formula (109) and having the empirical formula $C_{46}H38N_{12}Na_6O_{10}S_2$. 0.3 NaCl. 17 $H_2O$ gives:

Req. % C 35.9; H 4.71; N 10.92; S 4.16.
Found % C 36.0; H 4.7; N 10.9; S 4.1.

The compound having the formula (109) effects a significant reduction in whiteness and fluorescence of pre-brightened paper treated with said compound.

EXAMPLE 8

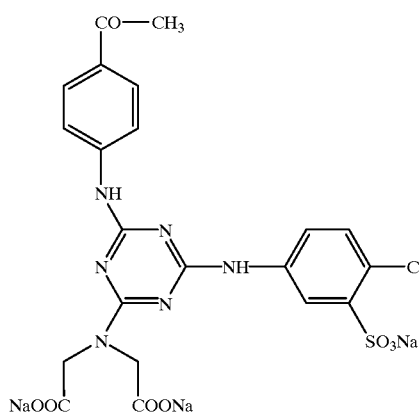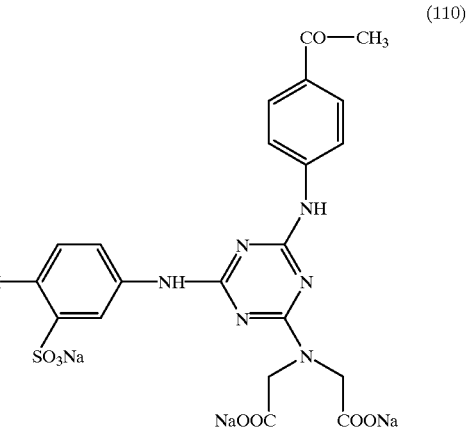

(110)

The compound of formula (110) is obtained in a yield of 87% of theory using the procedure described in Example 16, except that the L-glutamic acid is replaced by iminodiacetic acid.

Elemental analysis of the compound having the formula (110) and having the empirical formula $C_{44}H_{34}N_{12}Na_6O_{16}S_2 \cdot 0.8$ NaCl $\cdot 15$ $H_2O$ gives:

Req. % C 35.1; H 4.28; N 11.16; S 4.26.
Found % C 35.0; H 4.3; N 11.2; S 4.4.

The compound having the formula (110) effects a significant reduction in whiteness and fluorescence of pre-brightened paper treated with said compound.

EXAMPLE 9

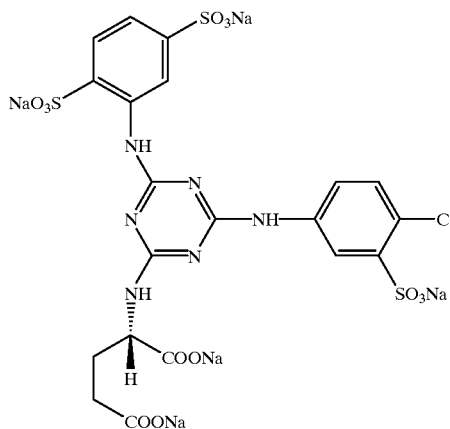

3.88 g of cyanuric chloride are dissolved in 50 mls of acetone and the solution is poured on to 20 g of ice. There is then added to this mixture, over 2 hours at 0° C., a solution of 5.32 g of aniline-2,5-disulfonic acid, dissolved in 30 mls of ice-water, the pH being held at 6 by the addition of sodium carbonate. To the reaction mixture so obtained, there are then added, dropwise at 30° C. over 1 hour, 3.7 g of the disodium salt of 4,4'-diamino-2,2'-stilbene disulfonic acid, dissolved in 50 mls of water, the pH being held at 6.5 by the addition of sodium carbonate. After the addition of 5.29 g of L-glutamic acid, the pH is adjusted to 8.5 and the acetone is distilled off from the reaction mixture over 5 hours at a bath temperature of 95° C. The free acid corresponding to the sodium salt of formula (111) is precipitated in acetone using HCl and the free acid so obtained is filtered off with suction. The filter residue is then dissolved in 100 mls of water and the solution is adjusted to pH 8.5. After evaporation and drying, there remain 17.5 g (67% theory) of the compound of formula (111).

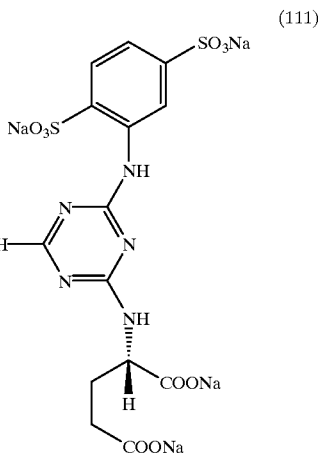

Elemental analysis of the compound having the formula (111) and having the empirical formula $C_{42}H_{30}N_{12}Na_{10}O_{26}S_6 \cdot 14.5$ NaCl $\cdot 18$ $H_2O$ gives:

Req. % C 18.6; H 2.45; N 6.2; S 7.09; Cl 18.9; $H_2O$ 11.9.
Found % C 18.6; H 2.50; N 6.2; S 7.0; Cl 19.0; $H_2O$ 11.6.

EXAMPLE 10

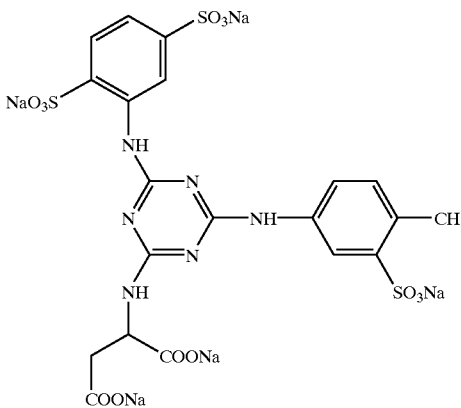

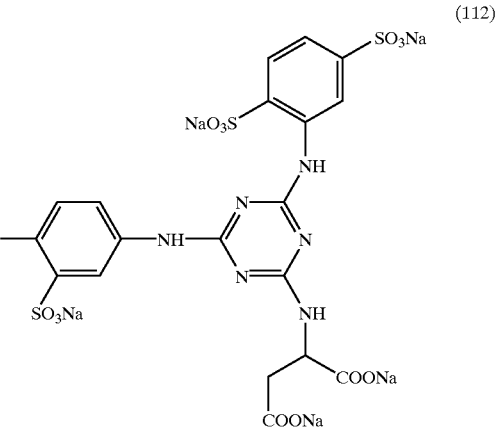

In a manner analogous to that described in Example 9, but replacing the L-glutamic acid used therein by the equivalent amount of D,L-aspartic acid, the compound of of formula (112) is obtained in 70% yield.

Elemental analysis of the compound having the formula (112) and having the empirical formula $C_{40}H_{26}N_{12}Na_{10}O_{26}S_6 \cdot 1.18\ NaCl\cdot 18\ H_2O$ gives:

Req. % C 25.2; H 3.27; N 8.81 S 10.08.

Found % C 25.2; H 3.3; N 8.8; S 9.9.

EXAMPLE 11

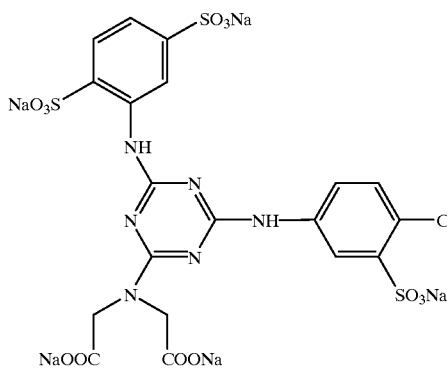
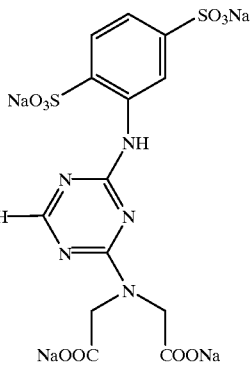

(113)

In a manner analogous to that described in Example 9, but replacing the L-glutamic acid used therein by the equivalent amount of iminodiacetic acid, the compound of of formula (113) is obtained in 60% yield.

Elemental analysis of the compound having the formula (113) and having the empirical formula $C_{40}H_{26}N_{12}Na_{10}O_{26}S_6 \cdot 1.41\ NaCl\cdot 24H_2O$ gives:

Req. % C 23.7; H 3.7; N 8.2 S 9.1.

Found % C 23.70; H 3.68; N 8.29; S 9.48.

EXAMPLES 12 TO 16

A coating composition is made up having the following composition:

40 parts of China clay
60 parts of calcium carbonate
9 parts of a styrene/butyl rubber latex
0.2 part of a polyvinyl alcohol and
0.25 part of a poly(acrylic acid)

The pH value of the coating composition is adjusted to 9.5 by adding the necessary amount of NaOH.

To separate portions of the coating composition, 0.2% or 0.4% (based on the total weight of China clay and calcium carbonate) of the fluorescent whitening agent (active substance) under test is added. The content of dry substance in the coating composition is adjusted to 60% by weight and the whole is stirred for 10 minutes. A base paper, which is free from wood and fluorescent whitening agent, is then coated with the coating composition, using a laboratory blade coater, at a coating weight of 11 g/m². After drying using IR radiation and hot air, the whiteness (CIE-Whiteness measured by SCAN-P 66:93) and brightness (ISO-Brightness measured by ISO 2470) of each coated paper sample are determined using a spectrophotometer. The fluorescence of each coated paper sample is determined from the difference between the respective whiteness and brightness values measured with and without UV in the light source.

The test fluorescent whitening agent compounds have the formula:

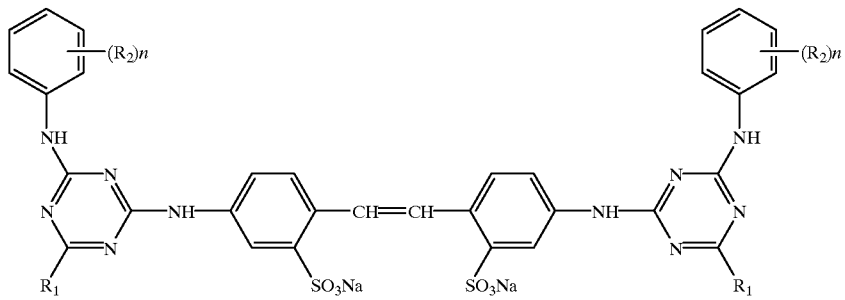

The test results obtained, using compounds having various substituents R, are set out in the following table 1.

TABLE 1

| Example | $R_1$ | $R_2$ | Whiteness 0.2% | Whiteness 0.4% | Brightness 0.2% | Brightness 0.4% | Fluorescence 0.2% | Fluorescence 0.4% |
|---|---|---|---|---|---|---|---|---|
| control | — | — | 70 | 70 | 84.4 | 84.4 | 0 | 0 |
| 12 | glutaric acid | H | 90 | 91 | 90.4 | 91.2 | 6.1 | 6.9 |
| 13 | D-aspartic acid | H | 91 | 93 | 90.9 | 91.8 | 6.4 | 7.3 |
| 14 | D,L-aspartic acid | 4-SO$_2$NH$_2$ | 88 | 87 | 90.3 | 90.4 | 5.9 | 6.1 |
| 15 | D,L-aspartic acid | 2,5-SO$_3$H | 85 | 85 | 88.9 | 89.6 | 4.6 | 5.2 |
| 16 | iminodi-acetic acid | 2,5-SO$_3$H | 86 | 84 | 89.5 | 89.2 | 4.9 | 5.0 |

The compound used in Example 13 is the compound of Example 2; the compound used in Example 14 is the compound of Example 3; the compound used in Example 15 is the compound of Example 10; and the compound used in Example 16 is the compound of Example 11.

The results in Table 1 demonstrate that coated paper samples produced according to the present invention have good whiteness, brightness and fluorescent properties.

EXAMPLE 17

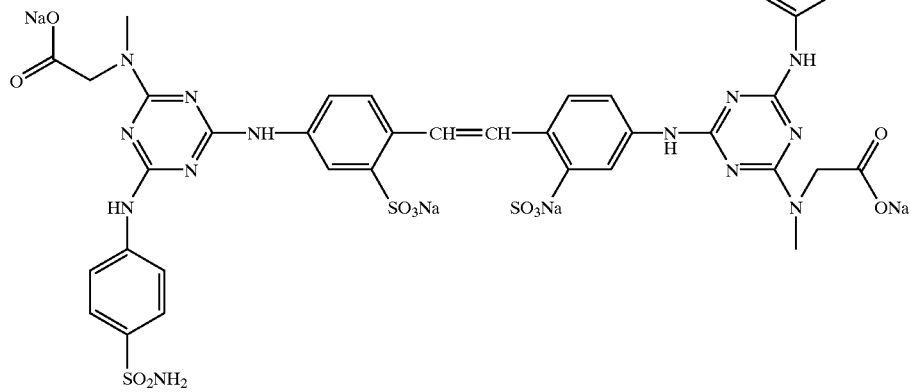

(114)

Using the procedure described in Example 3 but employing 5 g of the starting compound of formula (103) and reacting this with 1.8 g of a 40% solution of sarcosine, there are obtained 1.9 g of the compound of formula (114).

Elemental analysis of the compound having the formula (114) and having the molecular formula $C_{38}H_{34}N_{14}Na_4O_{14}S_4$ gives:

Req. % C 33.8; H 4.18; N 14.52; S 9.49.

Found % C 33.8; H 4.13; N 14.33; S 9.1.

EXAMPLES 18 TO 19

A standard (ECE) washing powder is made up from the following components in the indicated proportions (weight %):

| | |
|---|---|
| 8.0% | Sodium (C$_{11.5}$)alkylbenzene sulfonate |
| 2.9% | Tallow alcohol-tetradecane-ethylene glycol ether (14 mols EO) |
| 3.5% | Sodium soap |
| 43.8% | Sodium tripolyphosphate |
| 7.5% | Sodium silicate |
| 1.9% | Magnesium silicate |

-continued

| | |
|---|---|
| 1.2% | Carboxymethyl cellulose |
| 0.2% | EDTA |
| 21.2% | Sodium sulfate |
| 0 or 0.2% | compound (102) and Water to 100%. |

A wash liquor is prepared by dissolving 0.8 g. of the above washing powder in 200 mls. of tap water. 5 g. of cotton renforce are added to the bath and washed at 40° C. over 15 minutes and then rinsed, spin-dried and ironed at 160° C. This washing procedure is repeated three or ten times.

After the third and tenth washes, the whiteness of the washed samples is measured with a DCI/SF 500 spectrophotometer according to the Ganz method. The Ganz method is described in detail in the Ciba-Geigy Review, 1973/1, and also in the article "Whiteness Measurement", ISCC Conference on Fluorescence and the Colorimetry of Fluorescent Materials, Williamsburg, February 1972, published in the Journal of Color and Appearance, 1, No.5 (1972).

The Sun Protection Factor (SPF) is determined by measurement of the UV light transmitted through the swatch, using a double grating spectrophotometer fitted with an Ulbricht bowl. Calculation of SPF is conducted as described by B. L. Diffey and J. Robson in J. Soc. Cosm. Chem. 40 (1989), pp. 130–131.

The results obtained are set out in the following Table 2:

| Example | Test cpd. | Amount of test cpd. | Number of washes | Wash temp. ° C. | GW | SPF |
|---|---|---|---|---|---|---|
| — | none | — | 3 | 40 | 70 | |
| | | | 10 | 40 | 71 | 3 |
| 18 | cpd. (104) | 0.2% | 3 | 40 | 190 | |
| | | | 10 | 40 | 209 | 8 |
| 19 | cpd. (114) | 0.2% | 3 | 40 | 215 | |
| | | | 10 | 40 | 233 | 14 |

What is claimed is:

1. A method for the fluorescent whitening of a substrate comprising contacting the substrate with an effective whitening amount of a compound having the formula (1A):

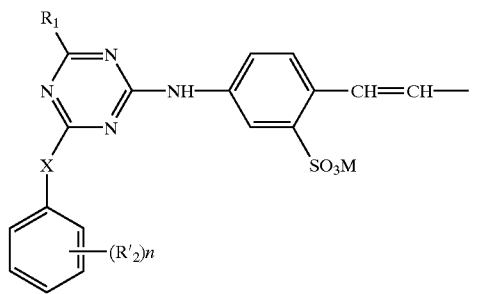

(1A)

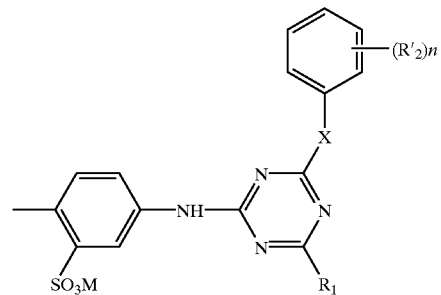

in which X is NH; M is hydrogen, an alkali metal atom, ammonium or a cation formed from an amine; each $R_1$, independently, is non-aromatic aminoacid residue from which a hydrogen atom on the amino group has been removed; n is 1 or 2; and each $R'_2$ independently, is hydrofen, $C_1$-$C_3$alkyl, halogen, cyano, COOR in which R is hydrogen $C_1$-$C_3$alkyl, COHN-R in which R has its previous signigicance, provided that those compounds are excluded in which X is NH, n is 2 and one $R'_2$ is $SO_3M$ in which M has its previous significance, and the other $R'_2$ is hydrogen, methyl or halogen.

2. A method according to claim 1 for the fluorescent whitening of a paper surface, comprising contacting the paper surface with a coating composition comprising a white pigment; a binder dispersion; optionally a water-soluble cobinder; and sufficient of a fluorescent whitening agent having the formula (1A) to ensure that the treated paper contains 0.01 to 1% by weight, based on the white pigment, of a fluorescent whitening agent having the formula (1A).

3. A method according to claim 2 in which the white pigment component of the paper coating composition is an inorganic pigment or a white organic pigment.

4. A method according to claim 3 in which the white pigment component is an aluminium or magnesium silicate, barium sulfate, satin white, titanium dioxide, clacium carbonate (chalk) or talcum.

5. A method according to claim 4 in which the binder consists of styrene/butyl acrylate or styrene/butadiene/acrylic acid copolymers or styrene/butadiene rubbers.

6. A method according to claim 2 in which the binder dispersion is a plastics dispersion based on copolymers of butadiene/styrene, acrylonitrile/butadiene/styrene, acrylic acid esters, acrylic acid esters/styrene/acrylonitrile, ethylene/ vinyl chloride and ethylene/vinyl acetate; or on homopolymers.

7. A method according to claim 2 in which the co-binder is present and is a water-soluble protective colloid which is soya protein, casein, carboxymethylcellulose, natural or modified starch, chitosan, or a derivative thereof, or polyvinyl alcohol.

8. A method according to claim 7 in which the colloid is a polyvinyl alcohol having a saponification level ranging from 40 to 100 and an average molecular weight ranging from 10,000 to 100,000.

9. A method according to claim 2 in which the paper coating composition used contains 10 to 70 % by weight of a white pigment; the binder is used in an amount which is sufficient to make the dry content of polymeric compound up to 1 to 30 % by weight of the white pigment; and the amount of fluorescent brightener of formula (1a) used is calculated so that the fluorescent brightener is present in an amount of 0.01 to 1% by weight, based on the white pigment.

10. A method according to claim 9 in which the binder is used in an amount which is sufficient to make the dry content of polymeric compound up to 5 to 25% by weight of the white pigment; and the amount of fluorescent brightener of formula (1a) used is calculated so that the fluorescent brightener is present in an amount of 0.05 to 1% by weight, based on the white pigment.

11. A method according to claim 2 in which the paper coating composition is prepared by mixing the components in any desired sequence at a temperature from 10 to 100° C.

12. A method according to claim 11 which the components also include customary auxiliaries which can be added to regulate the rheological properties of the coating compositions.

13. A method according to claim 12 in which the auxiliaries are natural binders, cellulose ethers, alginic acid, alginates, polyethylene oxide or polyethylene oxide alkyl ethers, copolymers of ethylene oxide and propylene oxide, polyvinyl alcohol, water-soluble condensation prosucts of formaldehyde with urea or melamine, polyphosphates or polyacrylic acid salts.

14. A method according to claim 1 for the fluorescent whitening of a paper surface comprising contacting the paper in the size press with an aqueous solution containing a size, optionally an inorganic or organic pigment and 0.1 to 20g/l of a fluorescent whitening agent having the formula (1A).

15. A method according to claim 14 in which the size is starch, a starch derivative or a synthetic sizing agent.

16. A method according to claim 1 for the fluorescent whitening of paper comprising adding the fluorescent whitening agent having the formula (1A) to and aqueous paper pulp in the wet end.

17. A process according to claim 1 in which M is hydrogen, Na, K, Ca, Mg, ammonium, mono-, di-, tri- or tetra-$C_1$-$C_4$alkylammonium, mono-, di- or tri-$C_1$-$C_4$hydroxyalkylammonium or ammonium that is di- or tri-substituted with a mixture of $C_1$-$C_4$hydroxyalkyl groups.

18. A process according to claim 1 in which n is 1 and $R_2$ is hydrogen, methyl, chlorine, cyano, COOH, COO-methyl, $CONH_2$, CONH-methyl, $SO_2NH_2$, or NH-CO-methyl.

19. A process according to claim 1 in which each of the aminoacid residues $R_1$ is the same and each has the formula -NH-CH($CO_2$H)-$R_3$ in which $R_3$ is hydrogen or a group having the formula -$CHR_4R_5$ in which $R_4$ and $R_5$, independently, are hydrogen or $C_1$-$C_4$alkyl optionally substituted by one or two substituents selected from the group consisting of hydroxy, thio, methylthio, amino, carboxy, sulfo, phenyl, 4-hydroxyphenyl, 3,5-diiodo-4-hydroxyphenyl, β-indolyl, β-imidazolyl and NH=C($NH_2$)NH-.

20. A process according to claim 1 in which the aminoacid from which the aminoacid residues $R_1$ are derived is glycine, alanine, sarcosine, serine, cysteine, histidine, α-aminobutyric acid, methionine, valine, norvaline, leucine, isoleucine, norleucine, arginine, ornithine, lysine, aspartic acid, glutamic acid, threonine, hydroxyglutamic acid or taurine, or a mixure or an optical isomer thereof.

21. A process according to claim 1 in which the aminoacid from which the aminoacid residues $R_1$ are derived is sarcosine, taurine, glutaric acid or aspartic acid.

22. A process according to claim 1 in which the aminoacid from which each aminoacid residue $R_1$ is derived is iminodiacetic acid.

\* \* \* \* \*